United States Patent
Lorkowski et al.

(10) Patent No.: US 11,301,038 B2
(45) Date of Patent: Apr. 12, 2022

(54) METHOD AND DEVICE FOR REDUCING MOVEMENT ARTEFACTS IN MAGNETIC RESONANCE IMAGING

(71) Applicant: Siemens Healthcare GmbH, Erlangen (DE)

(72) Inventors: Julian Lorkowski, Wayne, PA (US); Isabel Nieto Alvarez, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 90 days.

(21) Appl. No.: 16/682,642

(22) Filed: Nov. 13, 2019

(65) Prior Publication Data
US 2020/0150760 A1 May 14, 2020

(30) Foreign Application Priority Data
Nov. 13, 2018 (EP) .................................. 18205941

(51) Int. Cl.
G06F 3/01 (2006.01)
G06F 3/0482 (2013.01)
G06F 3/16 (2006.01)
G16H 30/20 (2018.01)
H04N 7/14 (2006.01)

(52) U.S. Cl.
CPC ............ *G06F 3/013* (2013.01); *G06F 3/0482* (2013.01); *G06F 3/167* (2013.01); *G16H 30/20* (2018.01); *H04N 7/147* (2013.01)

(58) Field of Classification Search
CPC ........ G06F 3/013; G06F 3/167; G06F 3/0482; G16H 30/20; H04N 7/147
See application file for complete search history.

(56) References Cited

U.S. PATENT DOCUMENTS

| | | | |
|---|---|---|---|
| 5,892,566 A | 4/1999 | Bullwinkel | |
| 6,774,929 B1* | 8/2004 | Kopp | A61B 5/055 345/8 |
| 10,286,179 B2 | 5/2019 | Giap et al. | |
| 2005/0273000 A1* | 12/2005 | Dinehart | A61B 5/055 600/410 |
| 2006/0277066 A1* | 12/2006 | Hungerford | G16H 40/67 705/2 |
| 2010/0231483 A1* | 9/2010 | Bazih | G01R 33/283 345/8 |
| 2010/0238362 A1* | 9/2010 | Hughes | A61B 5/0033 348/738 |

(Continued)

FOREIGN PATENT DOCUMENTS

WO 2015134953 A1 9/2015

OTHER PUBLICATIONS

European Search Report dated May 16, 2019, for Application No. 18205941.0.

*Primary Examiner* — Sang H Kim
(74) *Attorney, Agent, or Firm* — Banner & Witcoff, Ltd.

(57) ABSTRACT

A device configured to reduce movement artefacts in magnetic resonance (MR) imaging can include a head mount configured to hold a head of a patient on a patient bed of a magnetic resonance (MR) imaging system; a display; a supporting arm mechanically attached between mount and the display; an eye tracker configured to register one or more eye movements of the patient held in the head mount; and a controller configured to control content provided to the display.

25 Claims, 4 Drawing Sheets

(56) References Cited

U.S. PATENT DOCUMENTS

| | | | |
|---|---|---|---|
| 2013/0024208 A1* | 1/2013 | Vining | A61B 6/468 705/3 |
| 2015/0045654 A1* | 2/2015 | Lee | A61B 5/055 600/413 |
| 2015/0323617 A1* | 11/2015 | Ziarati | G01R 33/42 324/318 |
| 2016/0111021 A1* | 4/2016 | Knoche | G09B 7/00 434/262 |
| 2016/0252958 A1* | 9/2016 | Mizuhara | G06F 3/013 348/14.07 |
| 2017/0168124 A1* | 6/2017 | Ueda | H05B 47/105 |

* cited by examiner

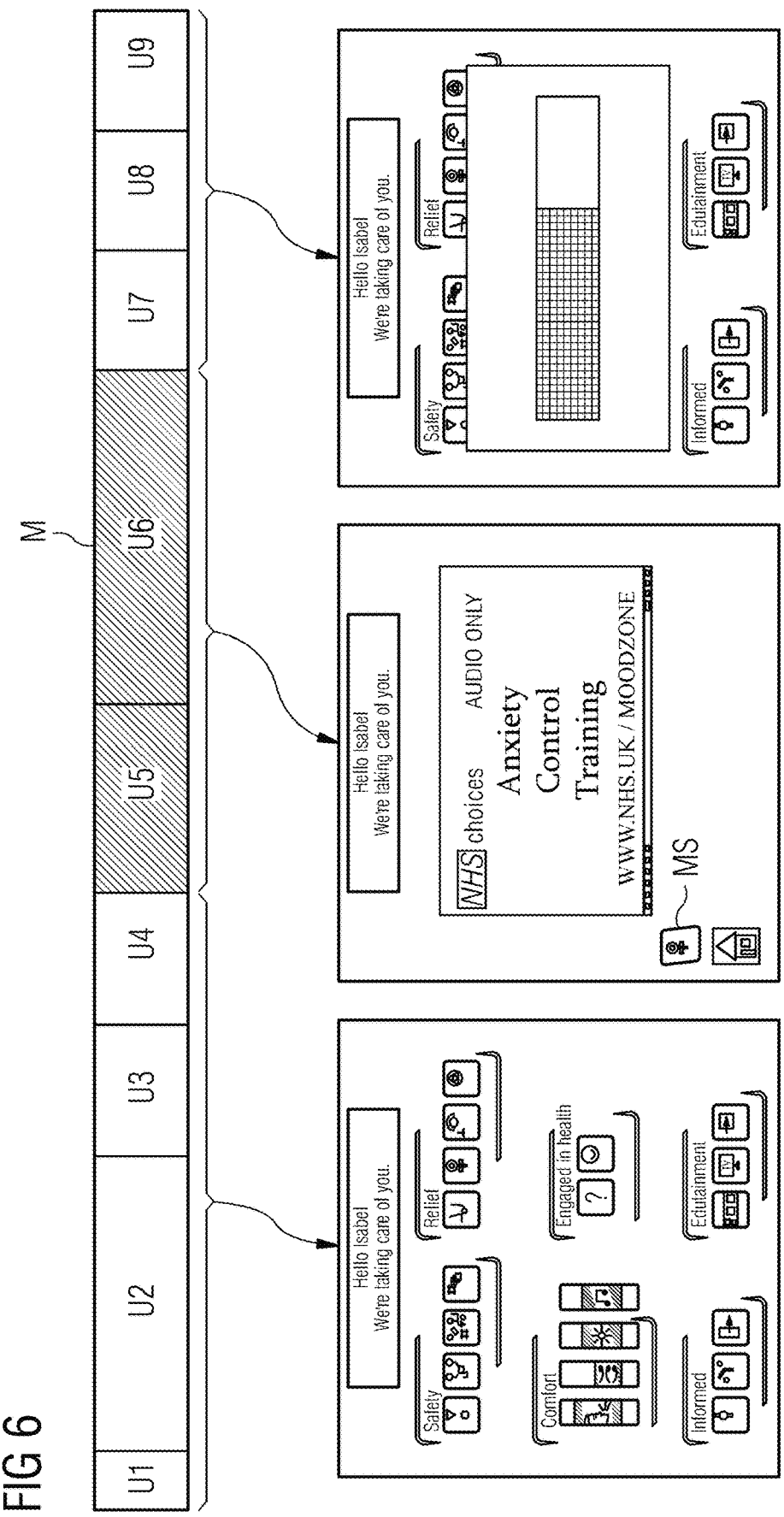

METHOD AND DEVICE FOR REDUCING MOVEMENT ARTEFACTS IN MAGNETIC RESONANCE IMAGING

CROSS REFERENCE TO RELATED APPLICATIONS

This patent application claims priority to European Patent Application No. 18205941.0, filed Nov. 13, 2018, which is incorporated herein by reference in its entirety.

BACKGROUND

Field

The disclosure describes a method and a device for reducing movement artefacts in magnetic resonance imaging, as well as a related magnetic resonance imaging system. The disclosure especially is advantageous for in-bore patient infotainment, reducing patient anxiety, increasing patient compliance, triggering patient engagement to health and reducing physiological stress reaction during examinations.

Related Art

In the technical field of magnetic resonance imaging (MRI), there occurs the problem that movements of a patient during magnetic resonance (MR) measurements can disturb the image quality due to movement artefacts.

During Magnetic Resonance ("MW") measurements it is important for a patient to lie motionless in the MR scanner, since movements during a measurement can lead to these image artefacts that can deteriorate the recorded image or even make it clinically unusable. This often results in repeated measurements which causes additional costs and is troublesome for the patient. The risk of movement artefacts increases especially in the case where very sick and elderly persons are examined, for whom it is harder to lie motionless in an MRI. Anxiety (e.g. claustrophobia) of the patient may result in body movement and, consequently, movement artefacts.

Additionally, anxiousness towards an imaging procedure or towards the clinical findings resulting from the procedure triggers a physiological stress response in the patient. A physiological stress response of the patient is associated with: reduced rational capacity thus reducing capacity to follow instructions and may result in patient not able to follow instructions during scan, reduced memory functionality which may result in patient having a limited ability to remember instructions before, during and after scan, increased respiratory rate which may result in complicating the acquisition of images, increased cortisol levels which may result in reducing the physiological immune response of the body potentially having an effect on disease progression.

There is one solution that, during an examination in a magnetic resonance imaging system, patients are connected through headphones to the voice of an MTRA (Medical Technical Radiology Assistant), which can provide information to the patient via audio (e.g. breathing commands). The MTRA may also provide further information to the patient, e.g. regarding the remaining time of an ongoing investigation. In particular, acoustic support can be given to motivate the patient not to move and thus avoid movement artefacts. However, the effect of this method depends on the motivation of the MTRA and is therefore subject to fluctuations.

However, there is also the possibility for broadcasting visual content of a monitor positioned at one end of the MRI to the patient via a mirror. As another solution, also a combination of visual and acoustic content is provided under the name "In-bore connect". However, moving inside the bore on the patient table is one of the anxiety triggers and currently there is no solution which addresses the patient once he/she lies down on the patient table.

A disadvantage of the prior art is that there is so far no optimal method and device that provides an effective way to manage a patient in an optimal way in order to reduce movements of the patient and especially reduce patient anxiety, increase patient compliance, trigger patient engagement to health and reduce physiological stress reaction. Therefore, until now there is no optimal solution to effectively reduce movement artefacts in MRI examinations.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

FIG. 6 shows an example operation of a patient interface according to an exemplary embodiment of the disclosure.

Figure 1:
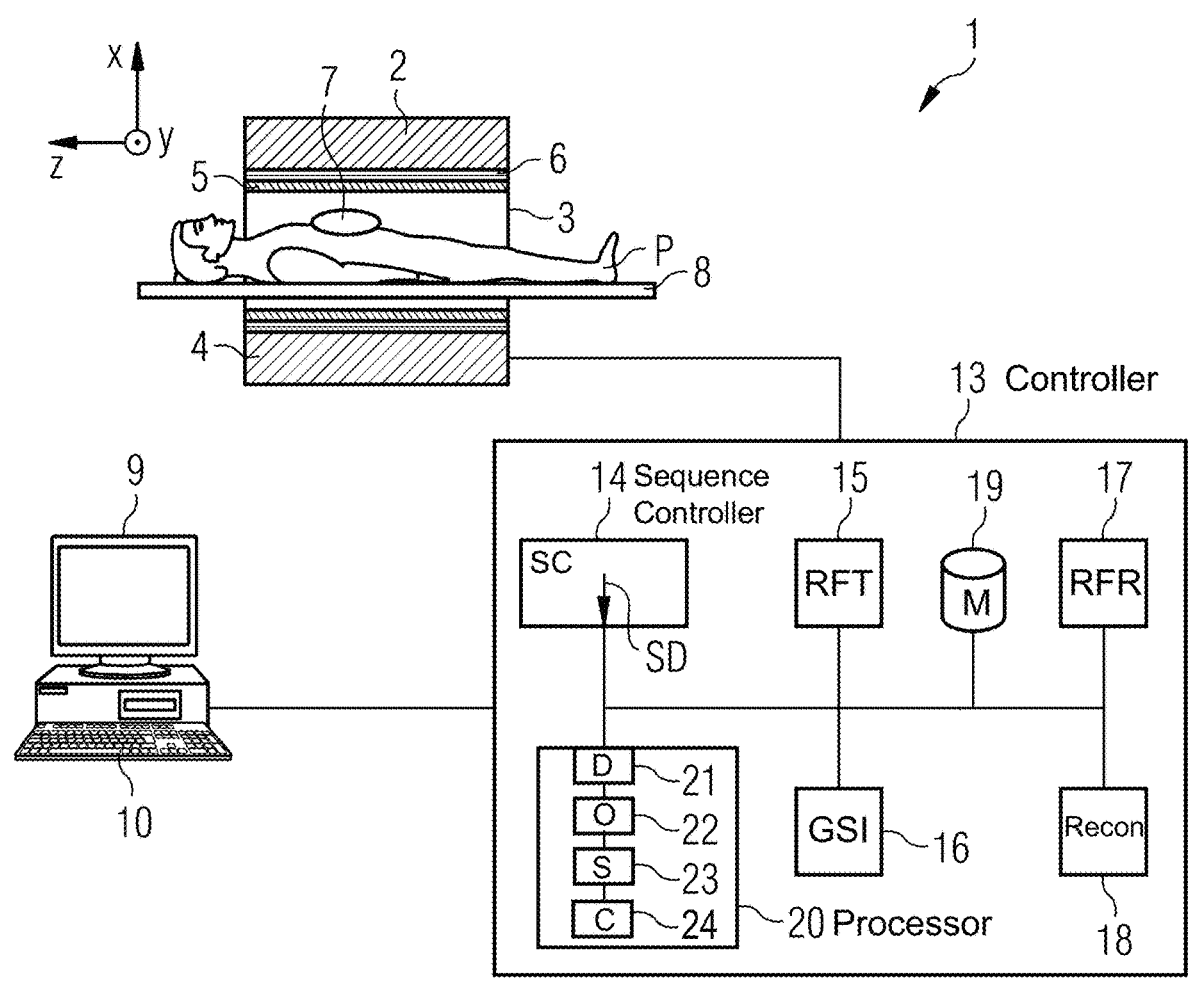
FIG. 1 illustrates an MRI system according to an exemplary embodiment.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure.

It is the object of the present disclosure to improve the known devices and methods to facilitate a reduction of movement artefacts in magnetic resonance imaging and especially reduce patient anxiety, increase patient compliance, trigger patient engagement to health, reduce physiological stress reaction and ease communication.

It has to be noted that a diagnostic examination is a traumatic experience with physiological implications for the individual. Addressing the needs of the individual already from the diagnostic point is of advantage for engagement in treatment.

In an exemplary embodiment, a device according to the disclosure for reducing movement artefacts in magnetic resonance imaging includes: a head mount, a display, support arm, eye tracker, and interface controller.

The head mount (head mount) is configured to hold (fix) a head of a patient. The head mount could be used to connect with the patient table in order to receive and send data from and to a computing system (controller) and/or in order to be mechanically fastened.

The display is configured to display images and/or videos to the patient and is the platform for interaction. The display can be a touchscreen display in one or more embodiments. In an exemplary embodiment, the functional electronics of the device are mounted in the housing of the display. In an exemplary embodiment, the display includes processor circuitry that is configured to display images and/or videos, detect one or more user inputs, and/or process detected input(s).

The supporting arm is configured as a mechanical attachment between the mount (head mount) and the display. In an exemplary embodiment, the support arm is attached to the head mount and is configured to hold the display in a (e.g. changeable) position. In an exemplary embodiment, the support arm is detachably and/or foldably attached to the head mount. In an exemplary embodiment, the support arm is formed as a protrusion from the head mount.

The eye tracker (eye sensor) is configured to register/detect and/or analyze eye movement of a patient lying in the head mount and to control the interface based on the detected eye movement (e.g. without other parts of the body moving). In an exemplary embodiment, the eye detector includes processor circuitry that is configured to detect and analyze eye movements, and generate one or more signals (e.g. control signals) corresponding to the detected and/or analyzed eye movements. In an exemplary embodiment, the eye tracker is mechanically aligned with the display, including, for example, having one or more measurement devices (e.g. cameras, sensors) at the border of the display and/or behind a (e.g. translucent or semi-translucent) display, so that eye movements of a patient are accurately measured. Since the head of the patient is normally arranged in the head mount, eye movements measured can be directly be registered in a coordinate system of the display.

In an exemplary embodiment, the eye tracker is configured to control the output of the display by the patient. The advantage of this technology, compared with others, e.g. voice control, is the minimization of movements that are necessary to control the display. In addition, this method is independent from loud measurement sequences. For example, a device controlled by voice could produce errors due to noise of the MRI-system or produce movement artefacts in the images caused by movements of the body due to spoken words (e.g. movements of the face or the diaphragm).

The controller is configured to control the content displayed or the analyzation of the eye movements to choose the content to be displayed. In an exemplary embodiment, the controller includes processor circuitry that is configured to perform one or more functions and/or operations of the controller. In an exemplary embodiment, the controller is comprised within the device, external to the device, or a combination thereof. For example, the device can be configured to work together with an external computing system connected with the device via an interface. Thus the device could include this interface designed for a data connection with an external computing system. In an exemplary embodiment, the internal controller is configured to communicate with an external computer/controller, where the internal and external controllers can cooperatively function to perform the functions described herein.

In an exemplary embodiment, with an external computing system, the analysis of the registered eye movements are at least partially processed by the external computing system. In this example, the external computing system and the device are configured to exchange data communications (e.g. the device could send data of the registered movements from the eye tracker to the computing system (via the interface)).

In an exemplary embodiment, the computing system of an MRI-system is used in connection with the device.

Advantageously, with the device according to the present disclosure, the patient can be provided with extensive information about many different technical fields, with visual input to address the human need of security and additionally be entertained. The patient could watch (and preferably also listen) to information about the actual examination, about the remaining examination time, and many more topics. The information and entertainment diverts the patient from the actual measurement and motivates the patient to lie motionless during the examination.

An aspect of the disclosure includes a method for reducing movement artefacts and especially reducing patient anxiety, increasing patient compliance, triggering patient engagement to health and reducing physiological stress reaction in magnetic resonance imaging, especially resulting from information or entertainment or a general distraction from the actual examination. In an exemplary embodiment, the method includes:

Determining the type of a section of a current examination sequence ("MR-section"). With the expression "type" a categorization is meant based on the influence of a certain MR-section on the patient, e.g. loudness, motion-sensitivity, length. For very loud or long MR-sections there might be the need for other information or entertainment than for relatively quiet or short MR-sections. Possible types could be preparation, pre-examination, loud section, long section, other characteristics or combinations of characteristics.

Sending a number of predefined menu items for displaying them on the display device, wherein the menu items are chosen depending on the determined type of a MR-section of an examination sequence. With this step, the number and type of the displayed menu items depends on the type of the actual MR-section of the examination sequence. However, a number of menu items could also be shown on the display device during the complete examination.

Selecting one of the menu items depending on the eye movements registered by the eye tracker.

In an exemplary embodiment, the controller according to the disclosure is configured to perform the method according to aspects of the disclosure. In an exemplary embodiment, the controlled is connected to the device via a (data) interface.

In an exemplary embodiment, a magnetic resonance imaging system according to the disclosure includes a device a controller, according to the disclosure. In an exemplary embodiment, the MRI system including the device according to aspects herein is configured to reduce movement artefacts in the measurements and especially reduce patient anxiety, increase patient compliance, trigger patient engagement to health and reduce physiological stress reaction.

In an exemplary embodiment, the controller includes one or more modules and/or units completely or partially realized as software running on a processor of the controller. A realization largely in the form of software modules can have the advantage that applications already installed on an existing system can be updated, with relatively little effort, to install and run these units of the present application. In an exemplary embodiment, the object of the disclosure is also achieved by a computer program product with a computer program that is directly loadable into the memory of a controller of an MRI-system or a computer, and which comprises program units to perform the steps of the inventive method when the program is executed by the controller. In addition to the computer program, such a computer program product can also comprise further parts such as documentation and/or additional components, also hardware components such as a hardware key (dongle etc.) to facilitate access to the software.

A computer readable medium such as a memory stick, a hard-disk or other transportable or permanently-installed carrier can serve to transport and/or to store the executable parts of the computer program product so that these can be read from a processor of a controller. A processor can include one or more microprocessors or their equivalents.

In an exemplary embodiment, the device includes a sound system, such as headphones. This has the advantage that the patient could listen to information or entertaining content in addition to the visual information of the display.

In an exemplary embodiment, the device includes a computing system configured to select content based on the eye movements registered by the eye tracker and output this content on the display device and/or the sound system. This computing system could be the same computing system mentioned above, however, this computing system could also be an additional computing system in the device that is responsible for the selection of content (e.g. menu items) shown on the display, wherein another (external) computing system that is connected to the device via said interface analyses the eye movements and provides extensive content to be displayed, e.g. videos. It is also possible that said computing system is an external computing system with a data-connection to the device that is now counted as part of the device.

In an exemplary embodiment, the controller includes:
A determiner that is configured to determine the type of a MR-section of a current examination sequence as already described above.
An output configure to send a number of predefined menu items for displaying them on the display device, wherein the menu items are chosen depending on the determined MR-section. As discussed herein, there could be the need for specific content chosen for a specific type of MR-section (e.g. depending on the loudness or length). It is predefined that a predefined choice, e.g. a menu item or a group of menu items, is shown on the display at the time certain types of MR-sections are applied. For example during very loud sections, there could be the choice for an active sound compression or a video showing a guidance for anxiety relief.
A selector configured to select one of the menu items depending on the eye movements registered by the eye tracker. The selector can be configured to analyze the registered eye movements.

In an exemplary embodiment, the device includes a communication module designed to establish a communication with another person based on the eye movements registered by the eye tracker, and preferably offer the possibility to select content items to the patient. This communication is meant to be at least a visual representation (e.g. live video broadcast) of another person. It could be a great relief for a patient, if a family member or friend could be seen during the examination. However, especially during periods where a little movement is possible, there could also be the possibility to establish an audio communication. At least it is advantageous for a patient if the voice of a beloved person could be listened to, even in the case the patient could not answer. This embodiment has the advantage that it addresses the human need for connection with others.

In an exemplary embodiment, the support arm is adjustable and/or the display device is adjustably attached to the supporting arm. It is especially preferred that the display device is movable relative to the head mount (especially by up to 90°) so that a patient is able to see the display device even in a sideward head position. Thus movement is preferably a shift and/or a rotational movement. It is further preferred that the supporting arm is detachable or foldable for an easy arrangement of a head in the mount.

Often patients are examined in different positions, where the face has to be arranged in different positions, as well. For example, the patient may lie on the back with face pointing up, the patient may lie on the side, head or feet could be pointing to the scanner. This embodiment allows an arrangement of the display where it could be seen by the patient. The supporting arm could preferably be rotationally connected on the front end of the head mount (where the top of the head of a patient is arranged) and could be turned in the right position if needed. It should be noted that the head mount should be designed such that an arrangement of the head in the actual measurement position is possible. Preferably, the head mount is formed such that a head of the patient could be mounted in different positions (e.g. with a variable bedding).

In an exemplary embodiment, the eye tracker is arranged on the supporting arm, at or in the display, such that the eye tracker can be moved together with the display.

In an exemplary method, by selecting one of the menu items predefined visual or acoustic information or a number of predefined sub-menu items is provided to the patient by the display and/or by the sound system. It should be noted that these sub-menu items are menu items, wherein the expression "sub-" only means that they are grouped under a superordinate menu item.

In an exemplary embodiment, the menu items or sub-menu items provide selectable information including:
Security, such as information concerning the used technology, the measuring device, the workflow of the examination and/or concerning arranging a help-call. This could be a live (video) call in the examination room and/or with a person involved in the examination or with a helping person, this could also be a video about the operation of the system or security-information.
Control, such as possibilities for controlling the display (brightness, contrast, the size of the menu icons or videos) and/or the sound system (e.g. loudness), the ventilation, the brightness or the temperature of the interior of the magnetic resonance imaging system.

General information, such as displaying a real time personal image or videos concerning anatomy and physiology or images taken by the magnetic resonance imaging system.

Entertainment, such as videos, music, television, games, an interface to the mobile phone of the examined patient.

Medical content, such as general medical information, information about the successful healing of other patients, recording questions for physicians.

Activity, such as information about the status of the examination, a to-do list, parameters of the actual measurement.

Communication, such as with the persons involved in the examination, family or friends.

Pain relief, such as visual training on pain management, live videocall with a physician.

Anxiety relief, such as visual training on respiration or stress management, live videocall with a health coach, meditation or spiritual videos.

In an exemplary embodiment, a further person (e.g. a physician) provides information on the display via an interface. This could be information about the next step of the examination, answers to questions of the patient or actual scan-specific information. In an exemplary embodiment, the physician is able to override the selection of the patient.

In an exemplary embodiment, the steps of the method are integrated in an MR-examination workflow.

FIG. 1 shows a schematic representation of a magnetic resonance imaging (MRI) system 1 according to an exemplary embodiment. In an exemplary embodiment, the MRI system 1 includes the actual magnetic resonance scanner (data acquisition unit) 2 with an examination space 3 or patient tunnel in which a patient P or test person is positioned on a driven bed 8, in whose body the actual examination object is located.

The magnetic resonance scanner 2 is typically equipped with a basic field magnet system 4, a gradient system 6 as well as an RF transmission antenna system 5 and an RF reception antenna system 7. In the shown exemplary embodiment, the RF transmission antenna system 5 is a whole-body coil permanently installed in the magnetic resonance scanner 2, in contrast to which the RF reception antenna system 7 is formed as local coils (symbolized here by only a single local coil) to be arranged on the patient P or test subject. In principle, however, the whole-body coil can also be used as an RF reception antenna system, and the local coils can respectively be switched into different operating modes.

The basic field magnet system 4 here is designed in a typical manner so that it generates a basic magnetic field in the longitudinal direction of the patient P, i.e. along the longitudinal axis of the magnetic resonance scanner 2 that proceeds in the z-direction. The gradient system 6 typically includes individually controllable gradient coils in order to be able to switch (activate) gradients in the x-direction, y-direction or z-direction independently of one another.

The MRI system 1 shown here is a whole-body system with a patient tunnel into which a patient P can be completely introduced. However, in principle the disclosure can also be used at other MRI systems, for example with a laterally open, C-shaped housing, as well as in smaller magnetic resonance scanners in which only one body part can be positioned.

Furthermore, the MRI system 1 has a central controller 13 that is used to control the MRI system 1. In an exemplary embodiment, the central controller 13 includes a sequence controller 14 configured to perform measurement sequence control operations. With this sequence controller 14, the series of radio-frequency pulses (RF pulses) and gradient pulses can be controlled depending on a selected MR-sequence M (see FIG. 2) or, respectively, a series of multiple MR-sequences M to acquire magnetic resonance images within a measurement session. For example, such a series of MR-sequences M can be predetermined within a measurement or control protocol. Different control protocols for different measurements or measurement sessions are typically stored in a memory 19 and can be selected by and operator (and possibly modified as necessary) and then be used to implement the measurement.

To output the individual RF pulses of an MR-sequence M, the central controller 13 has a radio-frequency transmission device 15 that generates and amplifies the RF pulses and feeds them into the RF transmission antenna system 5 via a suitable interface (not shown in detail). To control the gradient coils of the gradient system 6, the controller 13 has a gradient system interface 16. The sequence controller 14 communicates in a suitable manner with the radio-frequency transmission device 15 and the gradient system interface 16 to emit the MR-sequences M.

Moreover, the controller 13 has a radio-frequency reception device 17 (likewise communicating with the sequence controller 14 in a suitable manner) in order to acquire magnetic resonance signals (i.e. raw data) for the individual measurements, which magnetic resonance signals are received in a coordinated manner from the RF reception antenna system 7 within the scope of the MR-sequences M.

A reconstruction processor 18 receives the acquired raw data and reconstructs magnetic resonance image data therefrom for the measurements. This reconstruction is typically performed on the basis of parameters that may be specified in the respective measurement or control protocol. For example, the image data can then be stored in a memory 19.

Operation of the central controller 13 can take place via a terminal 10 with an input and a display 9, via which the entire MRI system 1 can thus also be operated by an operator. MR images can also be displayed at the display 9, and measurements can be planned and started by means of the input (possibly in combination with the display 9), and in particular suitable control protocols can be selected (and possibly modified) with suitable series of MR-sequences M as explained above.

The controller 13 includes a processor 20 configured to perform the method according to the disclosure. In an exemplary embodiment, the processor 20 includes the following components that may appear to be software modules.

A determiner 21 that is designed to determine the type of a MR-section U1, U2, U3, U4, U5, U6, U7, U8 of a current MR-sequence M (examination sequence, see FIG. 6).

An output 22 that is designed to send a number of predefined menu items M1, M2, M3, M4, M5, M6 (see FIG. 4) for displaying them on the display device 12 (see FIG. 3), wherein the menu items M1, M2, M3, M4, M5, M6 are chosen depending on the determined MR-section U1, U2, U3, U4, U5, U6, U7, U8.

Figure 3:
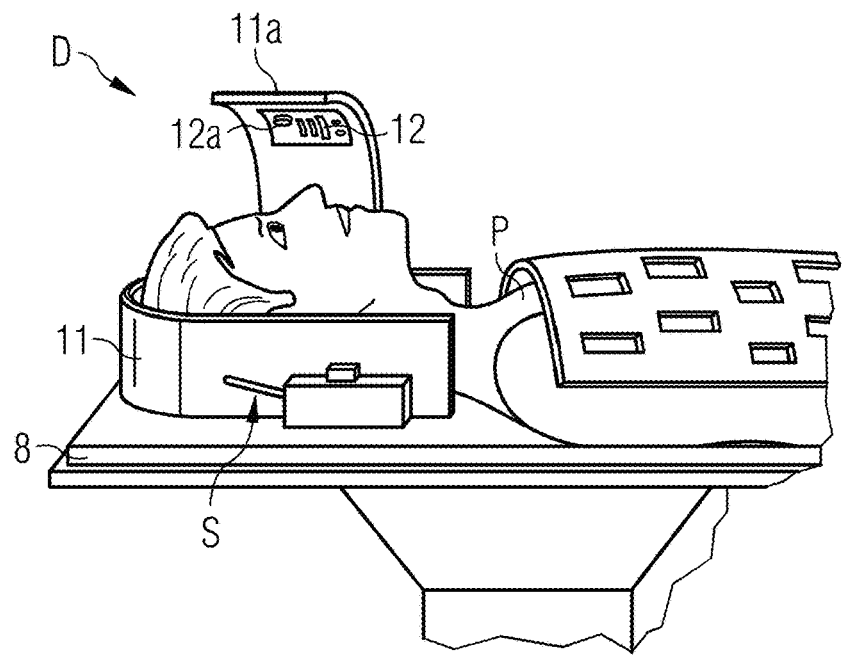
FIG. 3 shows a device according to an exemplary embodiment of the disclosure.

A selector 23 that is designed to select one of the menu items M1, M2, M3, M4, M5, M6 depending on the eye movements registered by the eye tracker 12a (see FIG. 3).

A communicator 24 configured to establish a communication with another person. In an exemplary embodiment, the communication is established based on the eye movements registered by the eye tracker. In an exemplary embodiment, the communicator 24 is configured to allow the other person to select content items for display to the patient. In an exemplary embodiment, the communicator 24 is a transceiver configured to establish communications via one or more wired and/or wireless communication protocols.

The MRI system 1 according to the disclosure, and in particular the controller 13, can have a number of additional components that are not shown in detail but are typically present at such systems, for example a network interface in order to connect the entire system with a network and be able to exchange raw data and/or image data or, respectively, parameter maps, but also additional data (for example patient-relevant data or control protocols). In an exemplary embodiment, the controller 13 (or one or more components therein) includes processor circuitry that is configured to perform one or more respective functions and/or operations of the controller 13 (or respective component(s)).

The manner by which suitable raw data are acquired by radiation of RF pulses and the generation of gradient fields, and MR images are reconstructed from the raw data, is known to those skilled in the art and thus need not be explained in detail herein.

Figure 2:
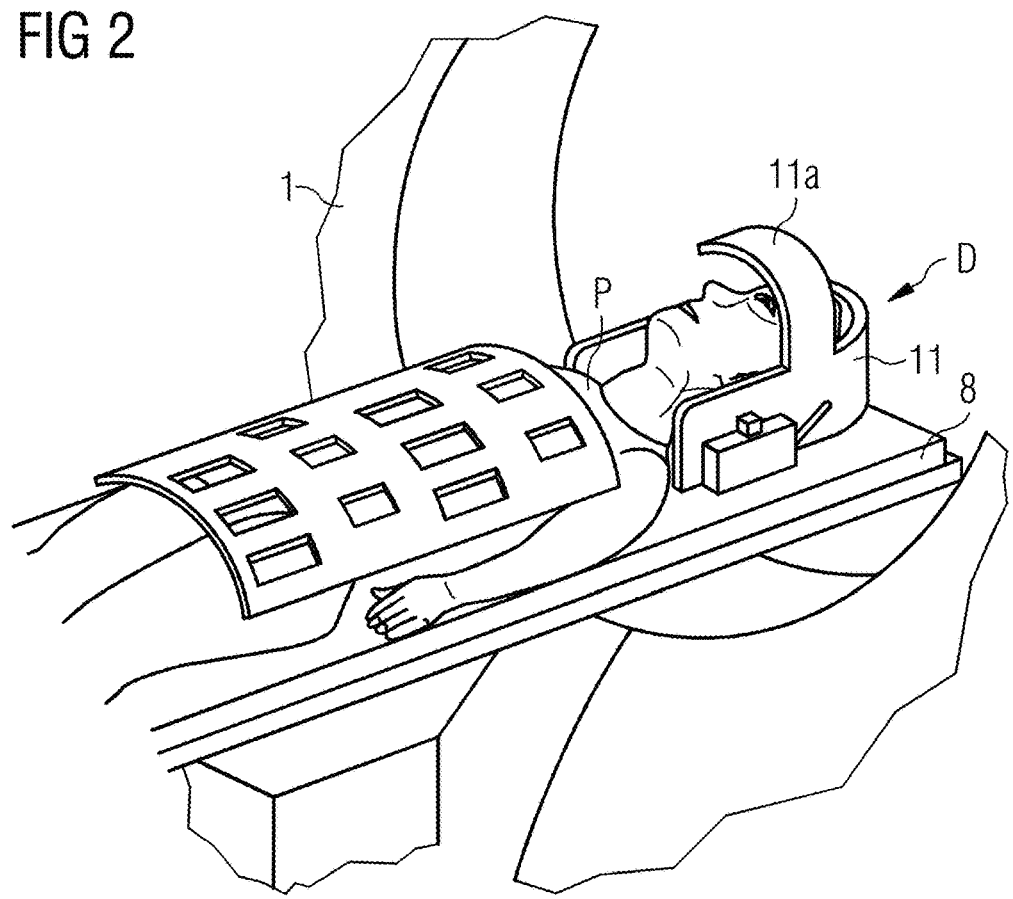
FIG. 2 shows the position of a device (e.g. patient support and interface) according to an exemplary embodiment of the disclosure.

FIG. 2 shows in a perspective view the position of a device D according to an exemplary embodiment, for reducing movement artefacts in magnetic resonance imaging according to the disclosure. The device D can be referred to as a patient support and interface. A patient P lying on a bed 8 is about to be examined in an MRI system 1, e.g. as shown in FIG. 1. The head of the patient P is mounted in a head mount 11 of the device D so that the head is held (or even fixed) during the examination. Over the head there is arranged a supporting arm 11a that may be a part of the head mount 11 or attached to the head mount 11.

FIG. 3 shows a perspective view of a device D according to an exemplary embodiment of the disclosure. Here the head of the patient P is shown from the side. In addition to the head mount 11 and the supporting arm 11a there is shown the display 12 where an eye tracker 12a is integrated. There could also be assumed that a sound system S is arranged in the device D, however, since headphones are preferred, the sound system S is in this example integrated in the head mount 11.

Figure 4:
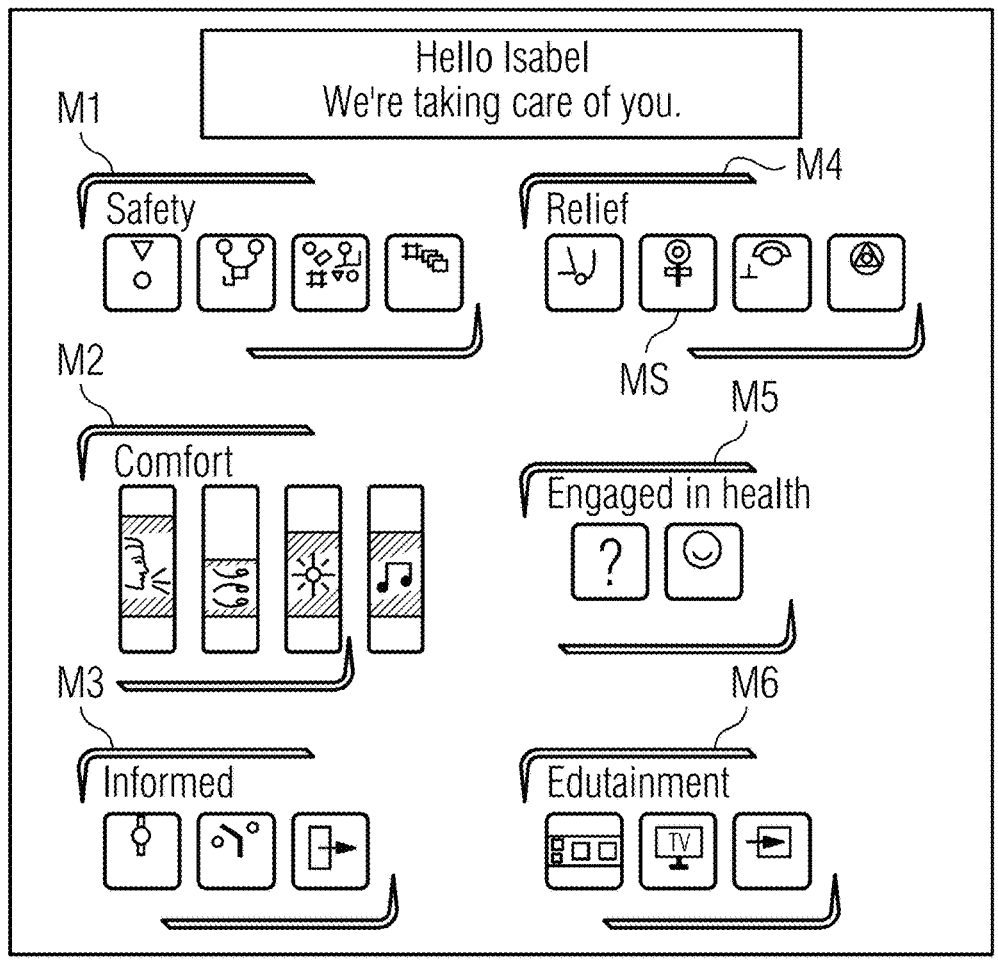
FIG. 4 illustrates a display interface according to an exemplary embodiment of the disclosure.

FIG. 4 illustrates an exemplary display view generated by the display 12 according to an exemplary embodiment of the disclosure. In this display view, there are arranged six menu items M1, M2, M3, M4, M5, M6 in groups of sub-menu items MS (for clarity, there is only the sub-menu item "anxiety relief" marked with a reference sign). The menu items M1, M2, M3, M4, M5, M6 (or the individual sub-menu items MS) could be selected by the patient, such as based on eye movement detection.

In an exemplary embodiment, in the first menu item M1, there are sub menu items concerning safety and connection. Here a trigger for help, a live videocall to the examination room and/or with a supporting person can be chosen.

In the second menu item M2 there are sub menu items concerning comfort. Here a control of the speaker volume, a control of the interior ventilation system and light and a selection of music can be chosen.

In the third menu item M3 there are sub menu items concerning information. Here the view of a real-time personal image, videos on anatomy and physiology and a request to send images directly can be chosen.

In the fourth menu item M4 there are sub menu items MS concerning anxiety and pain relief. Here a visual training on respiration, a visual training on stress management, a live videocall with a health coach and videos about meditation or spiritual issues can be chosen.

In the fifth menu item M5 there are sub menu items concerning the item "engaged in health". Here human connection, the recording of questions for a physician and videos about how other patients successfully healed can be chosen.

In the sixth menu item M6 there are sub menu items concerning entertainment. Here a selection of videos, games, TV (e.g. a news channel) and a (real-time) interface on the display 12 can be chosen.

Figure 5:
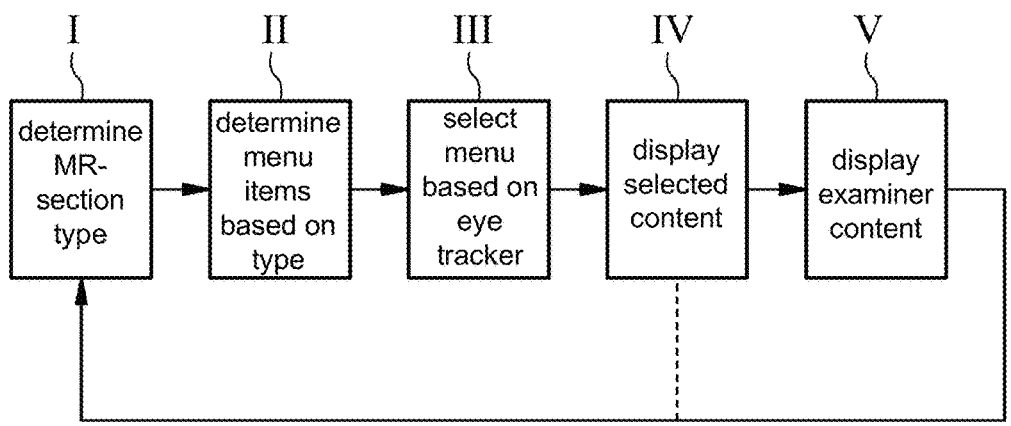
FIG. 5 shows a flowchart of a method according to an exemplary embodiment of the disclosure.

FIG. 5 shows a flowchart of a method according to an exemplary embodiment of the disclosure.

In step I, the type of a MR-section U1, U2, U3, U4, U5, U6, U7, U8 of a current examination sequence M (see FIG. 6) is determined.

In step II, a number of predefined menu items M1, M2, M3, M4, M5, M6 (see FIG. 4) is determined and provided for displaying them on the display 12 (see FIG. 3). In an exemplary embodiment, the menu items M1, M2, M3, M4, M5, M6 are chosen depending on the determined type of an MR-section U1, U2, U3, U4, U5, U6, U7, U8.

In step III, one of the menu items M1, M2, M3, M4, M5, M6 is selected by the patient. In an exemplary embodiment, the menu item is selected depending on the eye movements registered by the eye tracker 12a (see FIG. 3).

In step IV, content aligned with the selected menu item M1, M2, M3, M4, M5, M6 (or a group of sub-menu items MS) is output on the display 12. Then the process could return to step I again, as shown by the dashed line.

However, in the shown case, in step V, the examiner overrides the broadcast by adding new content, e.g. an actual image. Then the process returns to step I again and starts over.

FIG. 6 outlines an example operation of the patient interface in an MR examination procedure according to an exemplary embodiment. The MR examination can be, for example, a prostate examination, but is not limited thereto. The general principle is applicable to other measurement protocols for other clinical issues.

The shown MR measurement protocol includes an MR-sequence M with a number of different MR-sections U1, U2, U3, U4, U5, U6, U7. U8, U9. Each MR-section U1, U2, U3, U4, U5, U6, U7. U8, U9 is a measurement providing data that can be converted to an MR image and is characterized by a number of parameter values, e.g. concerning duration, loudness or the requirement of contrast agent administration. From the different characteristics of the different MR-sections U1, U2, U3, U4, U5, U6, U7, U8, U9 results the specific character of the whole MR measurement protocol MP. Depending on the clinical issue, the MTRA assembles various sequences into a protocol that can be used to produce sufficient data for MR images to answer the clinical question (here the condition of the prostate).

For example, some MR-sections U5, U6 are longer and/or louder than others. In the shown example, the louder MR-sections U5, U6 are marked with a hatched background. Depending on the character of the MR measurement protocols, specific software elements are now defined that are available to the patient P during the measurements and displayed on the screen. For example, during loud MR-sections U5, U6 there can be shown relaxing content on the display 12 or a special menu item M6 can be shown and chosen by the patient.

In the shown example, the patient has chosen the sub-menu item MS concerning anxiety and pain relief.

During a mainly quiet and long MR-section U2, for example, there can be assigned informative and entertaining content, wherein during mainly loud sections U5, U6, relaxing content could be selectable.

Although the present disclosure has been disclosed in the form of preferred embodiments and variations thereon, it will be understood that numerous additional modifications and variations could be made thereto without departing from the scope of the disclosure. For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A device configured to reduce movement artefacts in magnetic resonance (MR) imaging, comprising:
   a head mount configured to hold a head of a patient on a patient bed of a magnetic resonance (MR) imaging system;
   a display connected to the head mount by a supporting arm mechanically attached between the head mount and the display, a first end of the supporting arm being connected to the head mount and the display being supported on the support arm at a second end of the support arm opposite the first end;
   an eye tracker configured to register one or more eye movements of the patient held in the head mount; and
   a controller configured to:
      determine one or more MR-sections of a current examination sequence;
      determine a corresponding type of each of the one or more MR-sections; and
      provide one or more menu items for display on the display based on the determined corresponding type of the one or more MR-sections.

2. The device according to claim 1, further comprising an audio sound system configured to output audio to the patient.

3. The device according to claim 1, wherein the controller is configured to select content provided to the display based on the one or more eye movements registered by the eye tracker.

4. The device according to claim 1, wherein the controller comprises:
   a determiner configured to determine the corresponding type of the one or more MR-sections of the current examination sequence;
   an output configured to provide the one or more menu items for display on the display, wherein the one or more menu items are selected based on the determined corresponding type of the one or more MR-sections; and
   a selector configured to select a menu item of the menu items based on the eye movements registered by the eye tracker.

5. The device according claim 1, wherein the controller further comprises a communicator configured to establish a communication with another person based on the one or more eye movements registered by the eye tracker.

6. The device according claim 5, wherein the established communication is a video communication of the other person displayed on the display.

7. The device according to claim 1, wherein:
   the supporting arm is adjustable and/or the display is adjustably attached to the supporting arm,
   the display is movable relative to the head mount such that the display is viewable by the patient in a sideways head position, and the supporting arm is detachable, pivotable, and/or foldable for arrangement with respect to a head of the patent in the head mount.

8. The device according to claim 1, wherein the eye tracker is arranged on the supporting arm such that the eye tracker is movable together with the display.

9. The device according to claim 8, wherein the eye tracker is arranged adjacent to or in the display.

10. A method for reducing movement artefacts in magnetic resonance (MR) imaging, comprising:
   determining one or more MR-sections of a current examination sequence;
   determining a corresponding type of each of the one or more determined MR-sections;
   providing one or more menu items, from predefined menu items, for display on a display, based on the determined corresponding type of the one or more MR-sections; and
   selecting a menu item of the provided one or more menu items based on one or more eye movements of a patient under examination registered by an eye tracker.

11. The device according to claim 1, wherein the supporting arm is a cantilever supporting arm mechanically attached between the head mount and the display.

12. The device according to claim 1, wherein the corresponding type of the one or more MR-sections is based on a characteristic of the one or more MR-sections of the examination sequence.

13. The device according to claim 1, wherein the corresponding type of the one or more MR-sections is based on a loudness and/or a duration of the one or more MR-sections of the examination sequence.

14. The device according to claim 1, wherein the corresponding type of the one or more MR-sections includes: a preparation section, a pre-examination section, a loud or quiet section, and/or a long or short section of the examination sequence.

15. The device according to claim 1, wherein the controller is configured to determine the one or more MR-sections of the current examination sequence based on one or more characteristics of the current examination sequence.

16. The method according to claim 10, wherein, based on the selection of the menu item of the provided one or more menu items, providing predefined visual and/or acoustic information to the patient using the display and/or an audio system, or one or more predefined sub-menu items to the patient using the display.

17. The method according to claim 10, wherein the provided one or more menu items and/or one or more sub-menu items provide selectable information including: security information, control information, anatomic and/or physiological information, one or more images taken by the magnetic resonance imaging system, entertainment information, medical information, examination status information, communication information, pain relief information, and/or anxiety relief information.

18. The method according to claim 17, wherein:
   the security information includes a used technology, a measuring device being used, a workflow of the examination and/or arranging a help-call;
   the control information including information to control: the display and/or an audio system, ventilation, and/or brightness and/or temperature of an interior of the magnetic resonance imaging system;
   the anatomic and/or physiological information a real time personal image and/or a video on anatomy and physiology;
   the entertainment information including videos, music, television, games, and/or an interface to a mobile phone of the patient;
   the medical information about successful healing of other patients, and/or about recording questions for a physician;
   the examination status information includes information about a status of the examination, a to-do list, and/or one or more parameters of a measurement;
   the communication information includes information for communicating with one or more persons involved in the examination, one or more family members of the patient, and/or one or more friends of the patient;
   the pain relief information includes visual training information on pain management, and/or information for a live videocall with a physician; and
   the anxiety relief information includes visual training information on respiration or stress management, information for a live videocall with a health coach, and/or information for meditation and/or spiritual videos.

19. The method according to claim 10, further comprising providing, by information on the display by another person via an interface.

20. The method according to claim 10, wherein the method is integrated in an MR-examination workflow.

21. A computer program product having a computer program which is directly loadable into a memory of a controller of the magnetic resonance device, when executed by the controller, causes the magnetic resonance device to perform the method as claimed in claim 10.

22. A non-transitory computer-readable storage medium with an executable program stored thereon, that when executed, instructs a processor to perform the method of claim 10.

23. A magnetic resonance (MR) imaging system configured to reduce movement artefacts in MR imaging, comprising:
   a patient bed;
   a head mount disposed on the patient bed and configured to hold a head of a patient on the patient bed;
   a display connected to the head mount by a supporting arm mechanically attached to the head mount between the head mount and the display, a first end of the supporting arm being connected to the head mount and the display being supported on the support arm at a second end of the support arm opposite the first end;
   an eye tracker disposed on the supporting arm and configured to register one or more eye movements of the patient; and
   a controller configured to:
      determine one or more MR-sections of a current examination sequence;
      determine a corresponding type of each of the one or more MR-sections; and
      provide one or more menu items for display on the display based on the determined corresponding type of the one or more MR-sections.

24. The MR imaging system according to claim 23, wherein the controller is configured to select the content provided to the display based on the one or more eye movements registered by the eye tracker.

25. The MR imaging system according to claim 23, further comprising a magnetic resonance scanner configured to acquire one or more MR images.

* * * * *